(12) United States Patent
Sümegi

(10) Patent No.: US 6,656,955 B2
(45) Date of Patent: Dec. 2, 2003

(54) PHARMACEUTICAL COMPOSITION HAVING ENHANCED ANTITUMOR ACTIVITY AND/OR REDUCED SIDE EFFECTS, CONTAINING AN ANTITUMOR AGENT AND AN HYDROXIMIC ACID DERIVATIVE

(75) Inventor: Balázs Sümegi, Pécs (HU)

(73) Assignee: N-Gene Research Laboratories, Inc., New York, NY (US)

( * ) Notice: Subject to any disclaimer, the term of this patent is extended or adjusted under 35 U.S.C. 154(b) by 48 days.

(21) Appl. No.: 10/084,183

(22) Filed: Feb. 28, 2002

(65) Prior Publication Data

US 2002/0147213 A1 Oct. 10, 2002

Related U.S. Application Data

(62) Division of application No. 09/446,064, filed as application No. PCT/IB98/00961 on Jun. 22, 1998, now Pat. No. 6,440,998.

(30) Foreign Application Priority Data

Jun. 23, 1997 (HU) .............................................. 9701081

(51) Int. Cl.$^7$ ..................... A61K 31/445; A61K 31/335
(52) U.S. Cl. ....................................... 514/318; 514/449
(58) Field of Search .................................. 514/318, 449

(56) References Cited

U.S. PATENT DOCUMENTS

| | | | |
|---|---|---|---|
| 4,308,399 A | 12/1981 | Takacs et al. | 564/257 |
| 5,147,879 A | 9/1992 | Nagy et al. | 514/318 |
| 5,239,077 A | 8/1993 | Bertok et al. | 514/318 |
| 5,278,309 A | 1/1994 | Bertok et al. | 514/318 |
| 6,143,741 A | 11/2000 | Jednakovits et al. | 514/229.2 |

FOREIGN PATENT DOCUMENTS

WO    WO97/13504    4/1997

OTHER PUBLICATIONS

Watson S.A. et al, BIODRUGS, (1998) 9/4, (325–335).
Carter et al., Chemotherapy of Cancer, Second Edition, John Wiley & Sons, N.Y., N.Y., pp. 107–108, (Aug. 1981).

Primary Examiner—Jerome D. Goldberg
(74) Attorney, Agent, or Firm—Birch, Stewart, Kolasch & Birch, LLP

(57) ABSTRACT

The invention refers to pharmaceutical compositions suitable for the protection of the mitochondrial genome and/or mitochondrium from damages for the treatment of diseases connected with such damages, said compositions comprising a hydroximic acid derivative of formula I or a pharmaceutically acceptable acid addition salt therefor.

12 Claims, 3 Drawing Sheets

Figure 1:
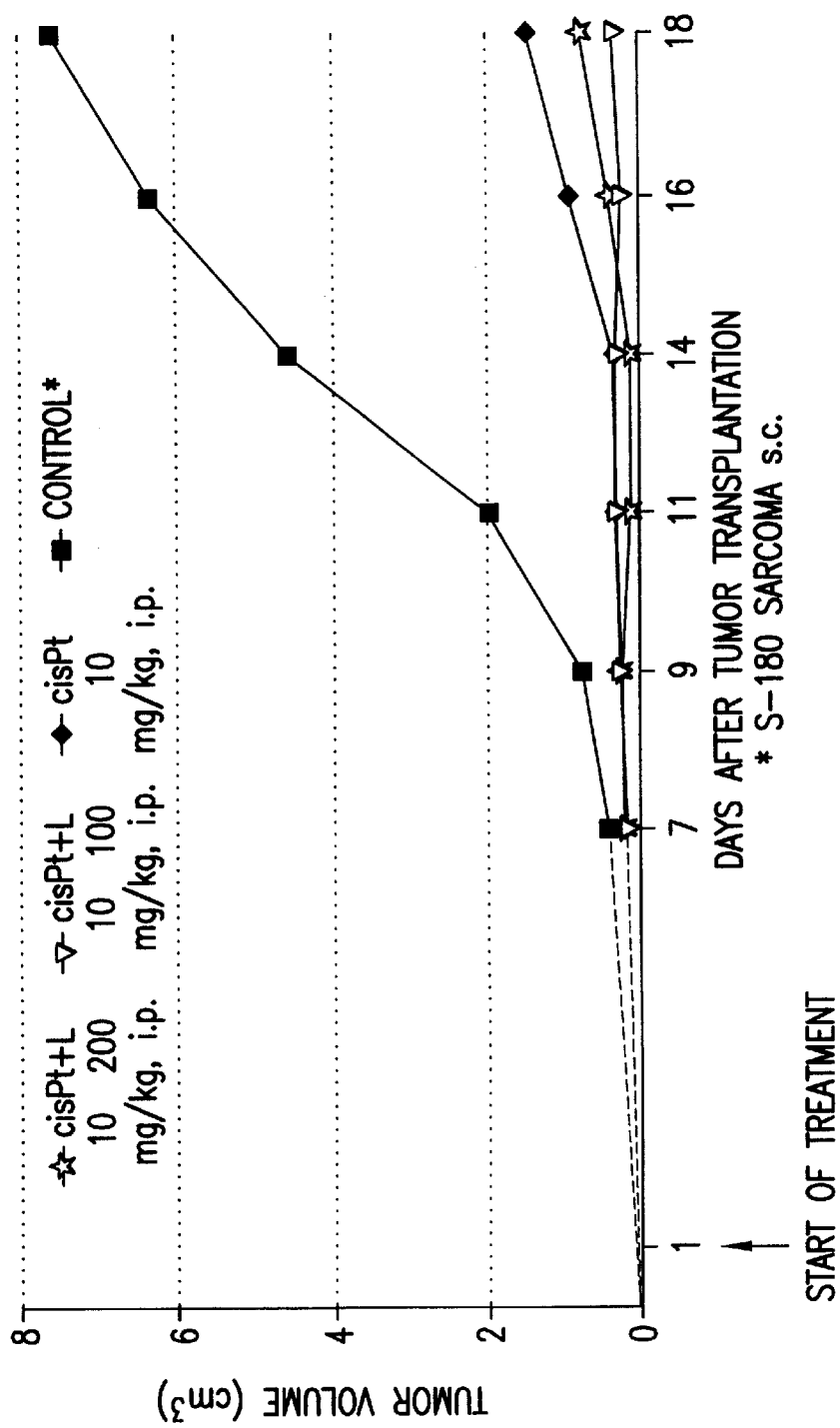

PHARMACEUTICAL COMPOSITION HAVING ENHANCED ANTITUMOR ACTIVITY AND/OR REDUCED SIDE EFFECTS, CONTAINING AN ANTITUMOR AGENT AND AN HYDROXIMIC ACID DERIVATIVE

This application is a divisional of co-pending application Ser. No. 09/446,064, filed on Feb. 17, 2000 now U.S. Pat. No. 6,440,498 B1 and for which priority is claimed under 35 U.S.C. §120. application Ser. No. 09/446,064 is the national phase of PCT International Application No. PCT/IB98/00961 filed on Jun. 22, 1998 under 35 U.S.C. §371. The entire contents of each of the above-identified applications are hereby incorporated by reference. This application also claims priority of application No. P97 01081 filed in Hungary on Jun. 23, 1997 under 35 U.S.C. §119.

The invention refers to a pharmaceutical composition having enhanced antitumor activity and/or reduced side effects.

A significant portion of antitumor agents (cytostatics) destroy tumor cells acting partially via inhibiting the synthesis of DNA and RNA, and partially via damaging the completed DNA. The known antitumour agents may seriously damage genes of healthy cells causing mutations and deletions both in the mitochondrial and the nuclear genoms. Antitumor agents often cause general cell damage besides their primary antitumor effect. This leads to side effects often making continuation of the treatment impossible, and even resulting in the death of patients. Therefore, the most critical part of antitumor treatment is the sensitivity of patient to the serious side effects of cytostatics.

Because of problems cited above, it is of great significance to produce pharmaceutical composition which possesses the antitumour activity of cytostatics or increased antitumor activity thereof without side effects or at least with reduced side effects.

The aim of the invention is to provide a pharmaceutical composition in which the activity of a known antitumor active substance is either enhanced, or said activity is retained and simultaneously the side effects of the known active substance are reduced.

Hydroximic acid derivatives of formula (I), $$R^3-A-\underset{\underset{B}{|}}{\overset{\overset{X}{|}}{C}}-\underset{\underset{}{}}{\overset{\overset{R}{|}}{N}}-O-CH_2-\overset{\overset{Y}{|}}{C}H-CH_2-N\overset{R^1}{\underset{R^2}{\diagdown}}$$ (I)

wherein $R^1$ is hydrogen or $C_{1-5}$alkyl group;

$R^2$ represents hydrogen; $C_{1-5}$alkyl group; $C_{3-8}$cycloalkyl group; or phenyl group optionally substituted by hydroxyl or phenyl group; or $R^1$ and $R^2$ together with the adjacent nitrogen atom form a 5 to 8 membered ring optionally containing additional nitrogen, oxygen or sulfur atom(s); and said ring can be condensed with an other alicyclic or heterocyclic ring, preferably with benzene, naphthalene, quinoline isoquinoline, pyridine or pyrazoline ring; furthermore if desired and it possible, nitrogen and/or sulfur as heteroatom(s) are present in the form of an oxide or dioxide;

$R^3$ stands for hydrogen or phenyl, naphthyl or pyridyl group optionally substituted by one or more halogen(s) or $C_{1-4}$alkoxy group(s);

Y is hydrogen; hydroxyl group; $C_{1-24}$alkoxy group optionally substituted by amino group; $C_{2-24}$polyalkenyloxy group containing 1 to 6 double bond(s); $C_{1-25}$alkenoyl group; $C_{3-9}$alkenoyl group; or a group of formula $R^7$—COO—, wherein $R^7$ is a $C_{2-30}$polyalkenyl group containing 1 to 6 double bond(s);

X represents halogen; amino group; or $C_{1-4}$alkoxy group; or

X and B together form an oxygen atom; or

X and Y together with the adjacent carbon atoms and the interjacent —NR—O—CH$_2$— group form a ring of formula (a), $$\underset{}{\overset{}{-}}\overset{\overset{|}{Z-CH}}{\underset{\underset{N-O}{\diagup}}{C}}\overset{}{\diagdown}CH_2$$ (a)

wherein

Z is oxygen or nitrogen;

R is hydrogen; or

R and B together form a chemical bond;

A stands for $C_{1-4}$alkylene group or a chemical bond; or a group of the formula (b), $$-(CH)_{\overline{m}}-(CH)_{\overline{n}}-\atop{\overset{|}{R^4}\phantom{xx}\overset{|}{R^5}}$$ (b)

wherein $R^4$ represents a hydrogen; $C_{1-5}$alkyl group; $C_{3-8}$cycloalkyl group; or a phenyl group preferably substituted by halogen. $C_{1-4}$alkoxy or $C_{1-5}$alkyl group;

$R^5$ stands for a hydrogen; $C_{1-4}$alkyl group; or a phenyl group;

m is 0, 1 or 2; and n is 0, 1 or 2 are known from the art.

The U.S. Pat. No. 4,308,399 discloses compounds belonging to the scope of hydroximic acid derivatives of formula (I), which are useful for treatment of the diabetic angiopathy.

The EP-PS No. 417,210 describes hydroximic acid halides, which also fall into the scope of compounds of formula (I), possess a selective β-blocking effect and are useful for treatment of the diabetic angiopathy.

HU-PS published under No. T/66350 discloses a number of other hydroximic acid derivatives being within the scope of compound of formula (I). These known substances are useful in the therapy of vascular deformations, particularly of diabetes mellitus.

It is known from the PCT Patent Application published under No. WO 97/13504 that hydroximic acid derivatives of formula (I) are useful for the prevention and treatment of disorders of mitochondrial origin.

The aim of the present invention is to provide a pharmaceutical composition possessing the effect of the known cytostatic agent but exerting the side effects thereof to a decreased degree.

It has been found that the above aim can be achieved by the pharmaceutical composition to the invention, which comprises a known cytostatic agent or, if desired and possible, a therapeutically useful acid addition salt thereof or therapeutically suitable salt thereof and a hydroximic acid derivative of formula (I), wherein R, $R^1$, $R^2$, $R^3$, A, B, X and Y are as defined above, or a therapeutically suitable acid addition salt thereof together with one or more usual carriers.

From the point of invention substituents defined in relation to the formula (I) are as follows:

$C_{1-5}$alkyl represents e.g. methyl, ethyl, n-propyl, isopropyl, n-butyl or n-pentyl group, preferably methyl or ethyl group;

$C_{3-8}$cycloalkyl is e.g. cyclopropyl, cyclopentyl, cyclohexyl, cycloheptyl or cyclooctyl group, preferably cyclopentyl or cyclohexyl group;

the 5 to 8 membered ring may be e.g. pyrrole, pyrazole, imidazole, oxazole, thiazole, pyridine, pyridazine, pyrimidine, piperazine, morpholine, indole or quinoline ring or the like;

the $C_{1-24}$alkoxy group may be e.g. methoxy, ethoxy, n-propoxy, tert-butoxy, n-pentoxy, decyloxy, dodecyloxy, octadecyloxy group or the like;

the $C_{1-25}$alkanoyl group may represent e.g. formyl, acetyl, propionyl, butyryl, caproyl, palmitoyl or stearoyl group and the like;

the $C_{3-9}$alkenoyl group means e.g. acryloyl, pentenoyl, hexenoyl, heptenoyl, octenoyl group or the like;

the $C_{1-4}$alkylene group may be e.g. methylene, ethylene, propylene or butylene group;

halogen is e.g. fluorine, chlorine, bromine or iodine, preferably chlorine or bromine.

Y as $R^7$—COO— group may be e.g. linolenyol, linoloyl, docosahexanoyl, eicosapentanoyl or arachidonoyl group or the like.

The physiologically (therapeutically) suitable acid addition salts of the compounds of formula (I) are meant to be acid addition salts formed with therapeutically suitable inorganic acids, e.g. hydrochloric or sulfuric acid and the like; or with therapeutically suitable organic acids, e.g. acetic, fumaric or lactic acid and the like.

With the compounds of formula (I), a preferable subgroup consists of hydroximic acid derivatives of formula (II),

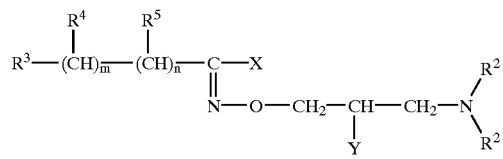

wherein $R^1$, $R^2$, $R^3$, $R^4$, $R^5$, m and n are as defined for formula (I), X means halogen or amino group; and Y stands for hydroxyl group.

Compounds of formula (II) wherein: $R^1$ and $R^2$ together with the adjacent nitrogen atom form a piperidino group; $R^3$ is pyridyl group; both m and n are 0; and X is as defined above, and particularly preferred. Of these:

O-(3-piperidino-2-hydroxyl-1-propyl)niconitic acid amidoxime dihydrochloride (compound "L") is especially suitable.

Another preferred group of the compounds of formula (I) consists of compounds of formula (III),

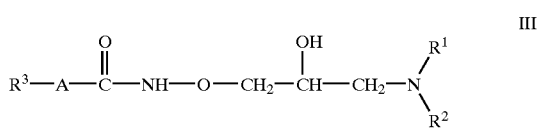

wherein $R^1$, $R^2$, $R^3$ and A are as defined for formula (I).

A third preferred subgroup of hydroximic acid derivatives of formula (I) includes cyclic compounds of formula (IV),

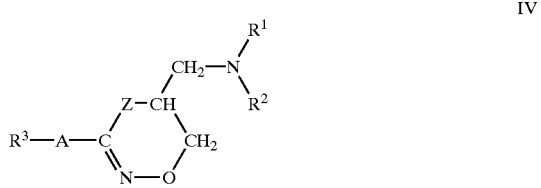

wherein $R^1$, $R^2$, $R^3$ and A are as defined for formula (I), and Z is oxygen or nitrogen.

A further preferred subgroup of hydroximic acid derivatives of formula (I) comprises compounds of formula (V),

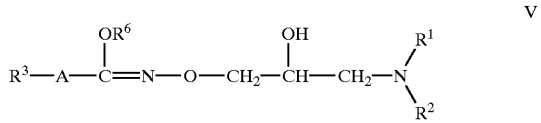

wherein $R^1$, $R^2$, $R^3$ and A are as defined in formula (I), and $R^6$ stands for $C_{1-4}$alkyl group.

The compounds of formula (I) can be prepared by using processes known from the U.S. Pat. No. 4,308,399, EP-PS No. 417,210; as well as from the published Hungarian Patent Application No. T/66350.

From the viewpoint of activity, a known cytostatic agent (substance) there is such an active agent, which directly or indirectly inhibits the DNA synthesis and/or transcription (RNA synthesis) and/or translation of the tumor cell; or injures the developed DNA.

A known pharmaceutical compound with antitumor activity is a compound which directly and/or indirectly inhibits the DNA synthesis and/or transcription (RNA synthesis)and/or translation, and damages the completed DNA in cancerous cell.

In detail, the known pharmaceutical compound with antitumor activity inhibits:
adenosine deaminase,
the biosynthesis of purine base and transformation of the nucleotidess,
biosynthesis of pyrimidine base,
reduction of ribonucleotides,
synthesis of thymidine monophosphate,
synthesis of RNA,
adduct of DNA,
synthesis of DNA,
damage of DNA,
synthesis of purine base and reduction of dihydrofolat,
protein synthesis and deamination of asparagine,
function of proliferation.

From the viewpoint of chemical structure, the known cytostatics may be:
alkylating agents comprising nitrogen-containing mustard derivatives, ethylene imine and methylmelamine derivatives; alkyl sulfonates; nitrosoureas; aziridines; triazenes and the like;

antimetabolites, within these folic acid analogues, pyrimidine analogues, purine analogues and the like;

native substances, including vinca alkaloids, podophyllotoxin, antibiotics and the like;

hormones including adrenocorticosteroids, estrogens, androgens, antiestrogens and the like; and other substances, such as complex forming agents.

From the known cytostatic active agents, e.g. preferred alkylating agents are as follows:

| | |
|---|---|
| Chlormethine: | 2-chloro-N-(2-chloroethyl)-N-methyl-ethanamine hydrochloride, |
| Mechlorethamine oxide: | 2-chloro-N-(2-chloroethyl)-N-methyl-ethanamine N-oxide, |
| Cyclophosphamide: | N,N-bis(2-chloroethyl)-tetrahydro-2H-1,3,2-oxazaphosphorin-2-amin-2-oxide, |
| Iphosphamide: | N,3-bis(2-chloroethyl)-tetrahydro-2H-1,3,2-oxazaphosphorin-2-amin-2-oxide, |
| Melfalan: | 4-[bis(2-chloroethyl)amino]-L-phenylalanine, |
| Chlorambucil: | 4-[bis(2-chloroethyl)amino]-phenylbutanoic acid, |
| Thiotepa: | triethylene-thiophosphoric acid amide, |
| Busulfan: | 1,4-butandiol dimethanesulfonate, |
| Carmustin: | 1,3-bis(2-chloroethyl)-l-nitrosourea, |
| Lomustin: | 1-(2-chloroethyl)-3-cyclohexyl-1-nitrosourea, |
| Semustin: | 1-(2-chloroethyl)-3-(4-methylcyclohexyl)-1-nitrosourea, |
| Improsulfan: | N,N-bis(3-methylsulfonyloxy-propyl)-amine, |
| Piposulfan: | 1,4-bis(3-methanesulfonyloxy-1-oxo--propyl)piperazine, |
| Benzodepa: | bisz(1-aziridinyl)phosphinylcarbamic acid phenylmethyl ester, |
| Meturedepa: | bis(2,2-dimethyl-1-aziridinyl)phosphinylcarbamic acid ethyl ester, |
| Uredepa: | bis(1-aziridinyl)phosphinylcarbamic acid ethyl ester, |
| Carboquone: | 2-[(2-aminocarbonyloxy)-1-methoxyethyl]--3,6-bis(1-aziridinyl)-5-methy-2,5-cyclohexadiene-1,4-dione, |
| Altretamine: | N,N,N',N', N",N"-hexamethyl-1,3,5-triazine-2,4.6-triamine, |
| Triethylene phosphoramide: | tris(1'-aziridinyl)phosphine oxide, |
| Trimethylolmelamine: | 2,4,6-tris(methylamino)-1,3,5-triazine, |
| Chlornaphazine: | N,N-bis(2-chloroethyl)-2-naphthylamine, |
| Cyclophosphamide: | N,N-bis(2-chloroethyl)-tetrahydro-2H--1,3,2-oxazaphosphorin-2-amine 2-oxide, |
| Estramustine: | estra-1,3,5(10)-triene-3,17-diol-3-[bis(2--chloroethyl)carbamate], |
| Novembichine: | 2-chloro-N,N-bis(2-chloroethyl)propane-amine hydrochloride, |
| Phenesterine: | Cholest-5-en-3β-ol-4-[bis(2-chloroethyl)-amino]-phenyl acetate, |
| Prednimustine: | 21-{4-[4-[bis(2-chloroethyl)amino]phenyl]-1-oxobutoxy}-11,17-dihydroxypregna-1,4--diene-3,20-dione, |
| Trophosphamide: | N,N,3-tris(2-chloroethyl)-tetrahydro-2H--1,3,2-oxazaphosphorin-2-amine 2-oxide, |
| Uracil-mustard: | 5-[bis(2-chloroethyl)amino]-2,4(1H,3H)-pyrimidinedione, |
| Chlorozotocin: | 2-[(2-chloroethyl)-nitrosoaminocarbonyl-amino]-2-deoxy-D-glucose, |
| Fotemustine: | [1-[(2-chloroethyl)-nitrosoaminocarbonyl-amino]ethyl]phosphonic acid diethyl ester, |
| Nimustine: | N'-[(4-amino-2-methyl-5-pyrimidinyl)-methyl]-N-(2-chloroethyl)-N-nitrosourea, |
| Ranimustine: | Methyl 6-[(2-chloroethyl)-nitrosoaminocarbonylamino]-6-deoxy-D-glucopyranoside |
| Mannomustine: | 1,6-bis(2-chloroethylamino)-1,6-dideoxy-D--mannitol dihydrochloride, |
| Mitobronitol: | 1,6-dibromo-1,6-dideoxy-D-mannitol, |
| Mitolactol: | 1,6-dibromo-1,6-dideoxygalactitol, |
| Pipobroman: | 1,4-bis(3-bromo-1-oxopropyl)-piperazine, |
| Decarbazine: | 5-(3,3-dimethyl-1-triazeno)imidazol-4-carboxamide. |

Preferred antimetabolites are e.g. as follows:

| | |
|---|---|
| Methotrexate: | N-[4-[(2,4-diamino-6-pteridinyl)methyl--methylamino]benzoyl]-L-glutamic acid or sodium salt thereof, |
| Trimetrexate: | 5-methyl-6-[(3,4,,5-trimethoxyphenyl)-aminomethyl]-2,4-quinazoline-diamine, |
| Fluroracil: | 5-fluoro-2,4(1H,3H)pyrimidinedione or sodium salt thereof, |
| Floxuridine: | 5-fluoro-2'-deoxyuridine, |
| Idoxuridine: | 5-iodo-2'-deoxyuridine, |
| Doxifluridine: | 5'-deoxy-5-fluorouridine, |
| Cytarabine: | 4-amino-1β-D-arabinofuranosyl-2(1H)-pyrimidinone, |
| Azacytidine: | 4-amino-1β-D-ribofuranosyl-1,3,5-triazin--2(1H)-one, |
| Gemcytabine: | 2',2'-difluoro-deoxycytidine, |
| Mercaptopurine: | 6-mercaptopurine, |
| Thioguanine: | 6-thioguanine, |
| Fludarabine phosphate: | 9β-D-arabinofuranosyl-2-fluoro-9H-purin--6-amine phosphate, |
| Pentostatine: | (R)-3-(2-deoxy-beta-D-erythro-pento-furanosyl)-3,6,7,8-tetrahidroimidazo[4,5-d][1,3]diazepin-8-ol, |
| Cladribine: | 2-chloro-deoxyadenosine, |
| Thiamiprine: | 6-(1-methyl-4-nitro-1H-imidazol-5-ylthio)--1H-purin-2-amine, |
| Ancitabine: | 2,3,3a,9a-tetrahydro-3-hydroxy-6-imino-6H-furo[2',3':4,5]oxazolo[3,2-a]pyrimidine-2-methanol, |
| Azacytidine: | 4-amino-1-beta-D-ribofuranosyl-1,3,5-triazin-2(1H)-one, |
| 6-Azauridine: | 2beta-D-ribofuranosyl-1,2,4-triazine-3,5-(2H,4H)-dione, |
| Carmofur: | 5-fluoro-N-hexyl-3,4-dihydro-2,4-dioxo--1(2H)-pyrimidine carboxamide, |
| Enocitabine: | N-(1beta-D-arabinofuranosyl-1,2-dihydro--2-oxo-4-pyrimidinyl)docosanamide, |
| Tegafur: | 5-fluoro-1-(tetrahydro-2-furanyl)-2,4(1H,3H)pyrimidinedione. |

From the known cytostatic active agents, e.g. the following substances of natural origin are favourable:

| | |
|---|---|
| Vinblastine sulfate: | vincaleucoblastine sulfate, |
| Vincristine sulfate: | 22-oxovincaleucoblastine sulfate, |
| Vindesine: | 3-(aminocarbonyl)-0-4-deacetyl-3-de-(methoxycarbonyl)-vincaleucoblastine sulfate, |
| Paclitaxel: | [2aR, 4S, 4aS, 6R, 9S (aiphaR, betaS), 11S, 12S, 12aR, 12bS]-beta-benzoylamino--alpha-(hydroxyphenyl)propionic acid [6,12b-bis(acetyloxy)-12-benzoyloxy-2a,3,4,4a,5,6,9,10,11,12,12a,12b-dodecahydro--4,11-dihydroxy-4a,8,13,13-tetramethyl-5--oxo-7,11-methano-1H-cyclodeca[3,4]benz[1,2-b]oxet-9-yl]ester, |
| Docetaxel: | [2aR-[2a alpha, 4 beta, 4a beta, 6 beta, 9 alpha (alphaR*, betaS*), 11 beta, 12 alpha, 12a alpha, 12a alpha, 12b alpha]]--beta-(tert-butoxycarbonylamino)-alpha--(hydroxyphenyl)propionic acid [12b-acetyl-oxy-12-benzyloxy-1,2,3,4,4a,6,9,10,11,12,12a,12b-dodecahydro-4,6,11-trihydroxy-4a,8,13,13-tetramethyl-5-oxo-7,11-methano--5H-cyclodeca[3,4]benz[1,2-b]oxet-9-yl]ester, |
| Etoposide: | [5R-[5 alpha, 5 alpha beta, 8a alpha, 9 beta-(R)]-[9-(4,6-0-ethylidene-beta-D--glucopyranosyloxy)-5,8,8a,9-tetrahydro-5--(4-hydroxy-3,5-dimethoxyphenyl)-furo |

| | -continued |
|---|---|
| Teniposide: | [3',4':6,7]naphtho[2,3-d]-1,3-dioxol-6-(5aH)-one,<br>[5R-[5 alpha, 5 alpha beta, 8a alpha, 9 beta-(R)]-[5,8,8a,9-tetrahydro-5-(4--hydroxy-3,5 -dimethoxyphenyl)-9-[4,6--O-(2-thienylmethylene)-beta-D-gluco-pyranosyloxy[furo 3',4':6,7]naphtho[2,3-d]--1,3-dioxol-6-(5aH)-one, |
| Dactinomycin: | actynomycin D, |
| Daunorubicin: | (8S-cis)-8-acetyl-10-(3-amino-2,3,6-trideoxy-alpha-L-lyxo-hexopyranosyloxy)-7,8,9,10-tetrahydro-6,8,11-trihydroxy-1-methoxy-5,12-naphthacenedione, |
| Doxorubicin: | (8S-cis)-8-(hydroxyacetyl)-10-(3-amino--2,3,6-trideoxy-alpha-L-lyxohexopyranosyl-oxy)-7,8,9,10-tetrahydro-6,8,11-trihydroxy--1-methoxy-5,12-naphthacenedione, |
| Epirubicin: | (8S-cis)-10-(3-amino-2,3,6-trideoxy-alpha--L-arabino-hexopyranosyloxy)-7,8,9,10--tetrahydro-6,8,11-trihydroxy-8-(hydroxy-acetyl)-1-methoxy-5,12-naphthacenedione, |
| Idarubicin: | (7S-cis)-9-acetyl-7-(3-amino-2,3,6-tri-deoxy-alpha-L-lyxo-hexopyranosyloxy)--7,8,9,10-tetrahydro-6,9,11-trihydroxy--5,12-naphthacenedione, |
| Mitoxantrone: | 1,4-dihydroxy-5,8-bis[2-(2-hydroxyethyl)a-mino-ethylamino]-9,10-anthracenedione or dihydrochloride thereof, |
| Bleomycin ($A_2$, $B_2$): | mixture of glycopeptide antibiotics isolated from Streptomyces verticillus species, mostly in the form of sulfate or hydrochloride, |
| Plicamycin: | an antibiotic produces by Streptomyces argillaceus, Streptomyces tanashiensis and Streptomyces plicatus, |
| Mitomycin: | [1aR-(1a alpha, 8 beta, 8a alpha, 8b alpha)]-6-amino-8-aminocarbonyloxa-methyl)-1,1a,2,8,8a,8b-hexahydro-8a-methoxy-5-methyl-azirino[2',3':3,4]-pyrrolo[1,2-a]indole-4,7-dione, |
| Aclacinomycin (A and B): | an antibiotic belonging to the anthracylin group, produced by Streptomyces galileus, |
| Anthramycin: | 3-(5,10,11,11a-tetrahydro-9,11-dihydroxy-8-methyl-5-oxo-1H-pyrrolo[2,1-c][1,4]-benzodiazepin-2-yl)-2-propeneamide, |
| Azaserine: | 0-diazoacetyl-L-serine, |
| Carubicin: | 8-acetyl-10-(3-amino-2,3,6-trideoxy-alpha-L-lyxo-hexopyranosyloxy)-7,8,9,10-tetra-hydro-1,6,8.11-tetrahydroxy-5,12-naphtha-cenedione, |
| Cactinomycin: | actinomycin C, an antibiotic produced by Streptomyces chrysomallus, |
| Carzinophilin: | an antibiotic produces by Streptomyces sahachiroi, |
| Chromomycin: | an antibiotic produced by Streptomyces griseus, |
| Olivomycin: | an antibiotic produced by Streptomyces olivoreticuli, |
| Nogalamycin: | [2R-(2 alpha, 3 beta, 4 alpha, 5 beta, 6 alpha, 11 beta, 13 alpha, 14 alpha)]-11-(6-deoxy-3-C-methyl-2,3,4-tri-0-methyl-alpha-L-mannopyranosyloxy)-4-dimethylamino-3,4,5,6,9,11,12,13,14,16-decahydro-3,5,8,10,13-pentahydroxy-6,13-dimethyl-9,16-dioxo-2,6-epoxy-2H-naphthaceno[1,2-b]oxocin-14-carboxylic acid methyl ester, |
| Peplomycin: | N'-[3-(1-phenylethyl)aminopropyl]-bleomycin amide, |
| Porfiromycin: | 6-amino-8-(aminocarbonyloxymethyl)-1,1a,2,8,8a,8b-hexahydro-8a-methoxy-1,5-dimethylazirino[2',3',:3,4]pyrrolo[1,2-a]in-dole- 4,7-dione, |
| Streptonigrin: | 5-amino-6-(7-amino-5,8-dihydro-6-methoxy-5,8-dioxo-2-quinolinyl)-4-(2-hydroxy-3,4-dimethoxy-phenyl)-3-methyl-2-pyridinecarboxylic acid, |
| Streptozocin: | 2-deoxy-2-(methyl-nitrosoamino-carbonylamino)-D-glucopyranose, |

| | -continued |
|---|---|
| Tubercidin: | 7beta-D-ribofuranosyl-7H-pyrrolo[2,3-d]-pyrimidine-4-amine, |
| Ubenimex: | [2S,3R]-3-amino-2-hydroxy-4-phenyl-butanoyl]-L-leucine, |
| Zorubicin: | benzoic acid [1-[4-(3-amino-2,3,6-triedoxy-alpha-L-lyxo-hexopyranosyloxy)-1,2,3,4,6,11-hexahydro-2,5,12-trihydroxy-7-methoxy-6,11-dioxo-2-naphthacenyl]-ethylidene]-hydrazide. |

From the known cytostatic active agents, the hormones described here are advantageous:

| | |
|---|---|
| Prednisolone: | (11-beta)-11,17,21-trihydroxypregna-1,4-diene-3,20-dione, |
| Hydroxyprogesterone: | 17-hydroxypregn-4-ene-3,20-dione or the caproate thereof, |
| Medroxiprogesterone: | (6 alpha)-17-hydroxy-6-methylpregn-4-ene-3,20-dione or the acetate thereof, |
| Megestrol: | 17-hydroxy-6-methylpregna-1,4-diene-3,20-dione or acetate thereof, |
| Diethylstilbestrol: | (E)-4,4'-(1,2-diethyl-1,2-ethenediyl)-bis(phenol), |
| Ethynylestradiol: | (17 alpha)-19-norpregna-1,3,5(10)-trien-20-yne-3,17-diol, |
| Tamoxifen: | (Z)-2-[4-(1,2-diphenyl-1-butenyl)phenoxy]-N,N-dimethylethanamine or the citrate thereof, |
| Testosterons: | (17-beta)-17-(1-oxopropoxy)-androst-4-ene-3-one or the propionate thereof, |
| Fluoximesterone: | (11-beta,17 beta)-9-fluoro-11,17-dihydroxy-17-methylandrost-4-ene-3-one. |

From the known cytostatic active agents preferred substances of other classes are e.g.:

| | |
|---|---|
| Cisplatin: | cis-diammine-dichloroplatinum, |
| Carboplatin: | cis-diammine-[1,1-cyclobutane-dicarboxylato(2)]-platinum, |
| L-Asparaginase: | an enzyme produced e.g. by Escherichia coli, |
| Procarbazine: | N-(1-methylethyl)-4-(2-hydrazino-methyl )benzamide, |
| Mitotane: | 1-chloro-2-[2,2-dichloro-1-(4-chlorophenyl)ethyl]benzene, |
| Flutamide: | 2-methyl-N-(4-nitro-3-trifluoromethyl-phenyl)propanamide, |
| Leuproreline: | 5-oxo-L-prolyl-L-histidyl-L-tryptophyl-L-seryl-L-tyrosyl-D-leucyl-L-leucyl-L-arginyl-N-ethyl-L-proline amide or acetate thereof. |

The known cytostatic active agent can be used also in the form of its therapeutically suitable acid addition salt, provided that its chemical structure allows the preparation of an acid addition salt. Similarly, the known cytostatic active agent may be used as its therapeutically suitable salt, e.g. metal salt, ammonium salt or salts formed with organic bases, when its chemical structure is suitable for the preparation of such salts.

The cytostatic pharmaceutical composition according to the invention contains preferably cisplatin as cytostatic (antitumor) active agent and O-(3-piperidino-2-hydroxy-1-propyl)nicotinic acid amidoxime or a therapeutically useful acid addition salt thereof as a hydroximic acid derivative of formula (I).

The pharmaceutical composition according to the invention usually contains the active agents (ingredients) in amounts of 0.1 to 95% by weight, preferably 1 to 50% by weight, preferably 5 to 30% by weight together with the usual carrier(s) of pharmaceutical compositions.

In the pharmaceutical composition according to the invention, the weight ratio of the two active ingredients (agents) is preferably (1 to 50):(50 to 1), particularly preferably (1 to 10):(10 to 1).

The pharmaceutical composition of the invention can be a solid or liquid composition useful for oral, parenteral or rectal administration or topical treatment.

The solid pharmaceutical compositions useful for oral administration can be powders, capsules, tablets, film-coated tablets, microcapsules and the like; and may contain as carrier(s) binders, e.g. gelatine, sorbitol, polyvinylpyrrolidone and the like; filling materials, e.g. lactose, glucose, starch, calcium phosphate and the like; tabletting aids such as magnesium stearate, talc, polyethylene glycol, silicon dioxide ant the like; as well as wetting agents. e.g. sodium lauryl sulfate and the like.

The liquid pharmaceutical compositions for oral administration are solutions, suspensions or emulsions containing as carriers e.g. a suspending agents, such as gelatine, carboxymethylcellulose and the like; emulsifying agents, e.g. sorbitan monooleate; solvents such as water, oils, glycerol, propylene glycol, ethanol; as well as preservatives such as methyl or propyl p-hydroxybenzoate and the like.

The pharmaceutical compositions for parenteral administration are usually the sterile solutions of the active agents.

The dosage forms (dosage units) exemplified above as well as other dosage forms are per se known, see e.g. the handbook entitled: Remington's Pharmaceutical Sciences, Edition 18, Mack Publishing Co., Easton, USA (1990).

In most cases, the pharmaceutical compositions according to the invention contain the dosage unit. For an adult person, the characteristic daily dose is 0.1 to 1000 mg of the known cytostatic active agent and 0.1 to 1000 mg of a compound of formula (I), which can be administered once or in more subdoses. The actual dose depends on several factors and is determined by the physician.

The pharmaceutical composition according to the invention is prepared by mixing the active agents (ingredients) with one or more carrier(s), then transforming the mixture obtained to a pharmaceutical composition in a manner known per se. The useful methods are known from the art, e.g. from the handbook of Remington's Pharmaceutical Sciences referred to.

I. Attenuating Side Effects of Cytostatics

The attenuating effect of hydroximic acid derivative of the formula I on the side effects of cytostatics was investigated by testing the hydroximic acid derivative compound "L". The experiments and results are being discussed below.

In vivo experiments with rats. Groups of 6 of Wistar rats were treated with cisplatin (50 mg/kg b.w. daily dose), and compound "L" (40 mg/kg b.w. daily dose), respectively administered separately and in combination. The animals were healthy (without any tumor inoculation) at the beginning of the experiment, and the dose of the antitumor compound was provocatively/unusually high which by itself would cause tissue damage with high probability. The control group did not receive either of the active compounds. During treatment, cardiac function of animals was followed by ECG, and after two weeks of treatment enzymatic activity in the blood of animals was determined. Concluding from the magnitude of the enzymatic activity, the extent of tissue damage caused by cisplatin was determined.

Investigation of Tissue Damage

Tissue damage was evaluated by measuring intracellular release of enzymes. Enzymatic activity was determined by the method of H. U. Bergmeyer. (Methods in Enzymatic Analysis, $2^{nd}$ edition, Academic Press (1974)/. The following enzymes were measured:

GOT=glutamate-oxalacetate-transaminase,
GPT=glutamate-piruvate-transaminase,
LDH=lactate dehydrogenase,
CK=creatine-kinase,
LipDH=lipoamide-dehydrogenase,
CS=citrate-synthase.

Enzymatic activity is given in mUnit/ml serum. Results are shown in Table 1.

TABLE 1

| | Enzymatic activity (mU/ml) | | |
|---|---|---|---|
| Enzymes | Cisplatin | cisplatin + "L" | control |
| GOT | 273 | 131 | 94 |
| GPT | 87 | 47 | 45 |
| LDH | 5136 | 1950 | 1523 |
| CK | 9776 | 1445 | 1200 |
| LipDH | 69 | 41 | 43 |
| CS | 22 | 8 | 6 |

As demonstrated in Table 1, enzymatic activity is increased by cisplatin treatment indicating tissue damage. When cisplatin and compound "L" were administered in combination, the enzymatic activity correlated well with that observed in the control group. Therefore, co-administration of compound "L" significantly protected against tissue damage caused by cisplatin.

Investigation of Cardiac Function

Cardiac function was monitored by AT-6 ECG on all four limbs. QRS, RR, PR and TQ distances and J point depressions were determined. Results are summarized in Table 2.

TABLE 2

| | J point depression mm | QRS ms | QRS intensity |
|---|---|---|---|
| Normal | 0.1 ± 0.1 | 67 | constant |
| Cisplatin | 2.1 ± 0.3 | 102 | fluctuating |
| Cisplatin + compound "L" | 0.3 ± 0.3 | 77 | constant |

As shown in Table 2, co-administration of compound "L" and cisplatin ensures significant protection against the cardiac function damaging effect of cisplatin. It should be noted, that fluctuation of QRS indicates significant cardiac damage due to cisplatin treatment, and this fluctuation ceased in the presence of compound "L".

One Month Survival After Treatment

It was investigated how many percent of animals were still alive following a two week treatment detailed above. Results are summarized in Table 3.

TABLE 3

| Treatment | One month survival (%) |
|---|---|
| Cisplatin | 25 |
| Cisplatin + compound "L" | 83 |
| Untreated | 100 |

As demonstrated in Table 3, only 25% of animals were alive following one month of treatment due to the extreme toxicity of cisplatin, whereas all untreated animals were alive. In contrast, 83% of animals which received cisplatin in combination with compound "L", were alive, i.e., death rate was low.

In vivo experiments with mice. Modulation of the systemic toxicity of the known cytostatic agent cisplatin (Platidiam, 50 La Chema, Brno) by compound "L" was studied in normal mice. [c.f. Oncology Report (REP/O.O.I./1988/01)]. First generation hybrid $BDF_1$ (C57B1 female× DBA/2 male) adult male mice, weighing 22–24 g, specified pathogen free (SPF) were used for these experiments. The animals were kept in macrolon cages at 22–24° C. (40–50% humidity), with a lighting regimen of 12/12 h light/dark. The animals had free access to tap water and were fed with a sterilized standard diet (Altromin 1324 pellets, Altromin Ltd, Germany) ad libitum. For toxicity testing compound "L", cisplatin and their mixture were dissolved in sterile physiological saline in a concentration that allowed the dose to be given in a volume of 0.1 ml/10 g body weight and administered i.p. or p.o.

Acute toxicological effect of compound "L", cisplatin, and compound "L"+cisplatin in combination Survival rates of $BDF_1$ male mice treated with different doses of compound "L", cisplatin, and compound "L"+ cisplatin in combination are summarized in Table 4.

Experiments with cell culture. Sp-2 (mouse myeloma, suspension) cells were plated on DMEM (Dubelso modified Eagle medium) in the presence of 10% FCS (fetal calf serum). Cells were plated on 96 hole plate with a starting cell number of $10^4/250$ μl.

One portion of cells were plated without the addition of drug, one portion of cells were plated in the presence of 0.35 microgram/ml cisplatin, another portion in the presence of 40 microgram/ml compound "L", still another portion in the presence of 0.35 microgram/ml cisplatin+40 microgram/ml compound "L" in combination. 48 hours after treatment, i.e., addition of the above listed compounds, cells in the holes were counted in a method of staining them with 10 microliter of tripaneblue following suspension. Counting was done in Burker chamber.

Effect on Tumor Growth

Table 6 summarizes the amount of cells surviving the treatment in percent.

TABLE 4

| Treatment Groups | Compound | Dose mg/kg | Route | Schedule | Survivors/ Total | Survival % |
|---|---|---|---|---|---|---|
| 1 | compound "L" | 200 | i.p. | 1 qd | 7/7 | 100 |
| 2 | compound "L" | 750 | i.p. | 1 qd | 0/7 | 0 |
| 3 | compound "L" | 2000 | p.o. | 1 qd | 7/7 | 100 |
| 4 | compound "L" | 100 | i.p. | 5 qd | 7/7 | 100 |
| 5 | cisPt | 10 | i.p. | 1 qd | 6/7 | 86 |
| 6 | cisPt | 15 | i.p. | 1 qd | 2/7 | 29 |
| 7 | cisPt | 4 | i.p. | 5 qd | 1/7 | 14 |
| 8 | compound "L" + cisPt | 500 + 10 | i.p. | 1 qd | 7/7 | 100 |
| 9 | Compound "L" + cisPt | 500 + 10 | i.p. | 1 qd | 6/7 | 86 |

The observation period was terminated after 25 days. Of compound "L" doses, the dose of 750 mg/kg body weight, i.p. was lethal (Table 4). Other single compound "L" treatments had no effect on the survival of BDF1 mice (Table 4). Dose dependent toxic effect of cisplatin was observed. The toxicity of cytostatic agent evaluated on the basis of survival was especially significant at higher dose and repeated treatments. The dose of 4 mg/kg, i.p., repeated 5 times (Sqd) was near lethal (Table 4). However, cisplatin (15 mg/kg, i.p.) in combination with compound "L" (500 mg/kg, i.p.) showed considerably reduced toxicity (Table 4).

When cisplatin was administered at dose of 10 mg/kg in combination with compound "L", all animals survived (Table 4).

II. Antitumor Activity

The antitumor effect of cytostatics in combination with hydroximic acid derivative of the formula I was investigated by testing the hydroximic acid derivative compound "L". The experiments and results are being discussed below.

TABLE 5

| Treatment | Surviving cell (%) |
|---|---|
| Untreated | 100 |
| Compound "L" | 51 ± 8 |
| Cisplatin | 12 ± 4 |
| Cisplatin + compound "L" | 10 ± 5 |

As demonstrated in Table 5, all untreated cells survive. Cisplatin by itself significantly reduces the number of tumor cells, and this effect does not change when cisplatin is added in combination with compound "L".

Similar effect was observed when the above experiment was repeated adding fluoroacil instead of cisplatin. In this case, one portion of cells were plated without the presence of drug, one portion of cells were plated in the presence of 13 microgram/ml fluoroacil, another portion in the presence of 13 microgram/ml fluoroacil+40 microgram/ml compound "L". Survival rate was examined 40 hours after treatment. Table 6 summarizes the amount of cells surviving the treatment in percent.

TABLE 6

| Treatment | Surviving cell (%) |
|---|---|
| Untreated | 100 |
| Compound "L" | 51 ± 8 |
| Fluoroacil | 13 ± 3 |
| Fluoroacil + compound "L" | 10 ± 4 |

As demonstrated in Table 6, fluoroacil by itself significantly reduces the number of tumor cells, and this effect remains unaffected when cisplatin is added together with compound "L". These in vitro experiments with antitumor agents (cisplatin or fluoroacil) by itself or in combination with compound "L" demonstrated that they excerted significant reduction of tumor cells in the cell culture. Thus, in vivo conditions, compound "L" did not influence the antitumor capacity of the investigated antitumor agents.

The above observations demonstrate that the pharmaceutical composition of formula I reduces the side effects of antitumor agents whereas their antitumor activity remains unaffected.

In vivo experiments with mice. Single or repeated treatments started on day 1 following transplantation of P-388 or S-180 tumor The therapeutic effectiveness was evaluated on the basis of survival time and tumor volume. The experiments were terminated after 45 days. Long-term survival of mice were not followed beyond 45 days, but the end point was on day 46 following tumor transplantation. The comparative antitumor effect of various treatment groups on the median survival time in days for treated versus control groups was expressed as T/C.

In the case of S-180 solid tumor the tumor growth inhibitory effect of compounds was controlled 3 times for a week using digital caliper. Tumor volume was calculated using the following formula:

$$V = a^2 \times b^2 \times \pi / 6$$

where "a" and "b" are the shortest and the longest diameter, respectively of a given tumor (Tomayko M. M. and Reynolds C. P.: Determination of subcutaneous tumor size in athymic/nude/mice. Cancer Chemother. Pharmacol, 24, p. 148,1989). Mean values (X) and standard deviations (S.D.) were calculated. The statistically significant difference (p) was determined by Student' t test, where appropriate.

Influence of Compound "L" in vivo on the Antitumor Activity of Cytostatic Agent Cisplatin The effect of cisplatin by itself or in combination with compound "L"÷cisplatin on the survival of BDF1 mice inoculated with 1×106 P-388 leukemia cells is shown in Table 7.

TABLE 7

| Treatment Groups[1] | Compound | Treatments[2] | | | Mean Survival (days) | T/C % | Long term[3] | |
|---|---|---|---|---|---|---|---|---|
| | | Dose mg/kg | Route | Schedule | | | Survivors/ Total | Percent survival |
| 10 | CisPt | 10 | i.p. | 1 qd | 16.6 ± 4.6/ 5 mice | 147.0 | 2/7 | 29 |
| 11 | CisPt + compound "L" | 10 + 100 | i.p. | 1 qd | 32.6 ± 3.5/ 5 mice | 289.0 | 2/7 | 29 |
| 12 | CisPt + compound "L" | 10 + 200 | i.p. p.o. | 1 qd | 19.0 ± 3.9/ 4 mice | 168.0 | 3/7 | 43 |
| 13 | CisPt | 3 | i.p. | 5 qd | 29.0 ± 6.1/ 4 mice | 257.0 | 3/7 | 43 |
| 14 | CisPt + compound "L" | 3 + 20 | i.p. | 5 qd | 30.0/ 1 mouse | 266.0 | 6/7 | 86 |
| 15 | Control (P-388) | — | — | — | 11.3 ± 1.2/ 7 mice | 100.0 | — | — |

Treatments started 1 day after the i.p. tumor transplantation. These experiments were terminated on day 45 and the number of long-term survivors is shown in Table 7. As demonstrated in Table 7, the effectiveness of cisplatin increased in the presence of compound "L". Although, compound "L" could also considerably elevate the mean survival time when administered in combination with cisplatin, this combination was particularly effective after repeated administration especially concerning the long-term survival (i.e., up to 45 days). The long-term survival of P-388 tumor bearing mice treated with compound "L"+ cisplatin was 86% relative to control value (0%). However, the long-term survival of mice treated with cisplatin by itself was only 43% to control group (Table 7).

Figure 2:
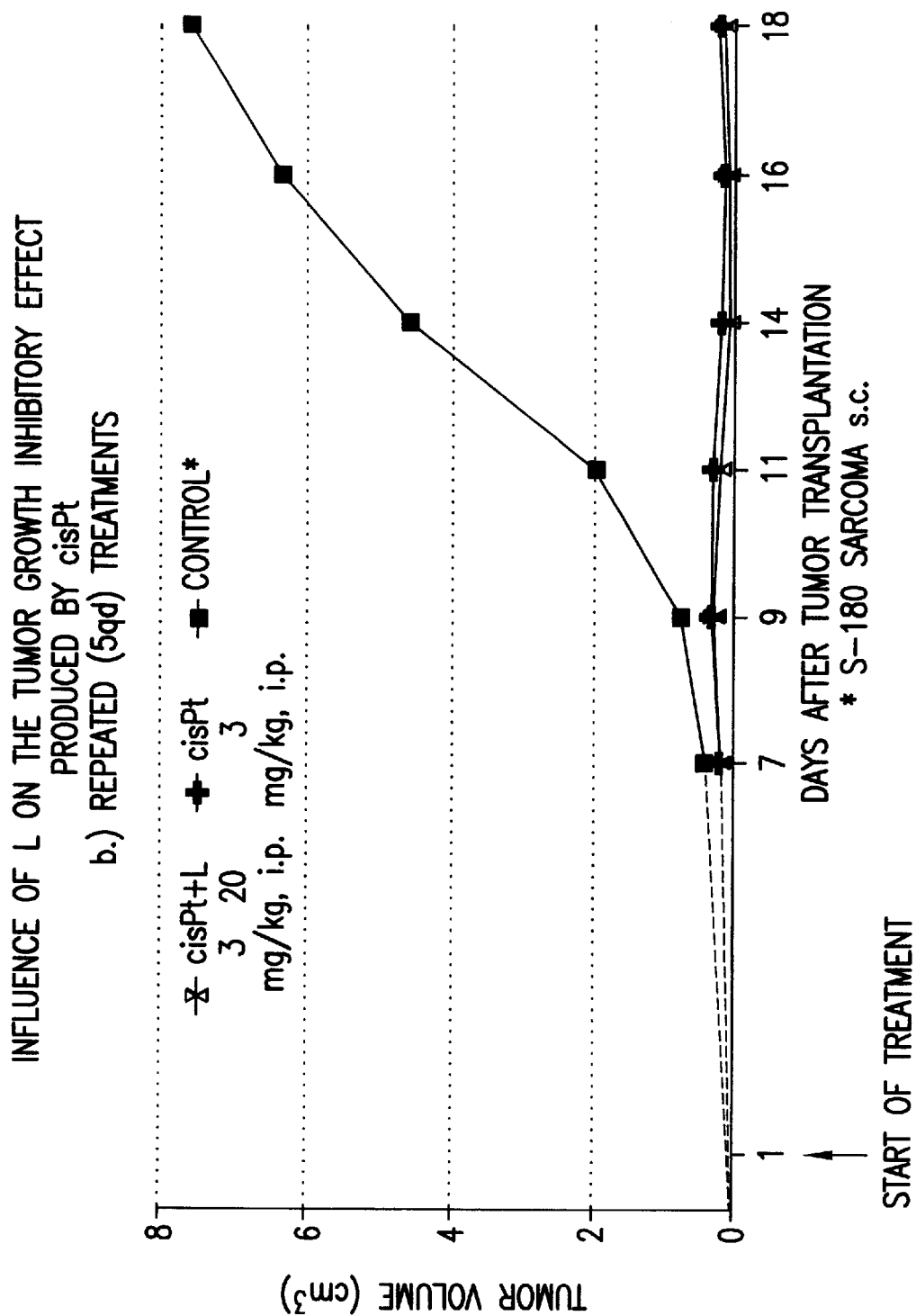

Influence of Compound "L" on the Tumor Growth Inhibitory Effect of Cisplatin Against S-180 Sarcoma On the basis of tumor growth curves and mean tumor volumes, a significant inhibitory effect of cisplatin and the compound "L"+cisplatin combination was observed following single (FIG. 1.) or repeated injections (FIG. 2.).

Figure 3:
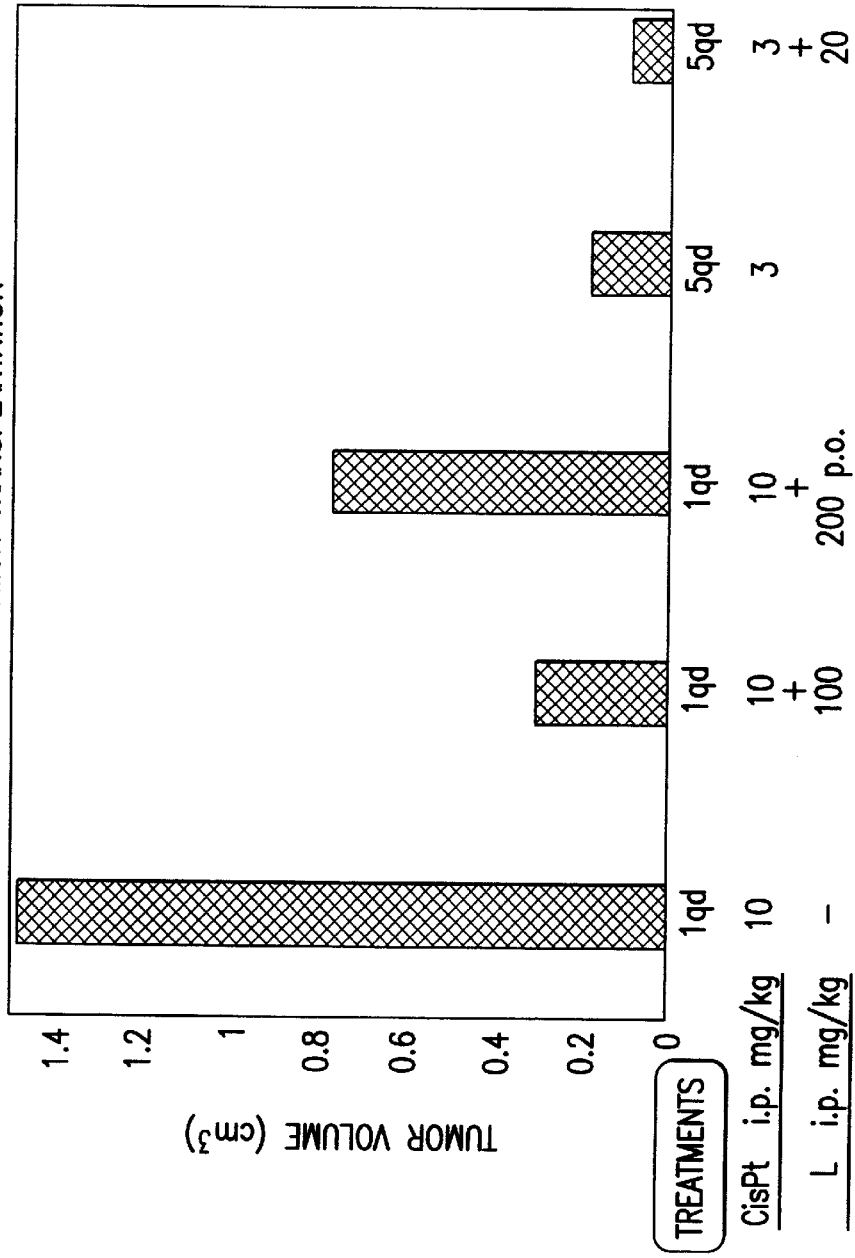

The tumor growth inhibitory effect of cisplatin in comparison with mixture of compound "L" plus cisplatin on day 18 after tumor transplantation is illustrated in FIG. 3. Presence of compound "L" increased the tumor growth inhibitory effect of cisplatin significantly (FIG. 3.).

The pharmacological compound of the invention proved to be very safe (i.e., unusually non-toxic even in tumor-bearing animals), and can be used for increasing the effectiveness and reducing the side effects of antitumor treatment of cancer patient during which the patient is treated with a known antitumor compound or its pharmaceutically acceptable acid addition salt supplemented by a hydroximic acid derivative of the formula I or a pharmaceutically acceptable acid addition salt thereof in (1–50):(1–50)% by mass.

What is claimed is:

1. A pharmaceutical composition having antitumor activity with reduced side effect(s) comprising an enhanced effective amount of a known active substance having antitumor effect selected from the group consisting of paclitaxel and docetaxel and an effective amount of a hydroximic acid derivative of the formula I

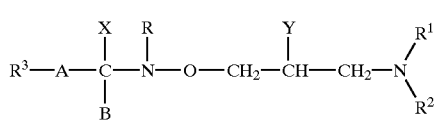
(I)

wherein $R^1$ represents a hydrogen atom or a $C_{1-5}$ alkyl group, $R^2$ stands for a hydrogen atom, a $C_{1-5}$ alkyl group, a $C_{3-8}$ cycloalkyl group or a phenyl group optionally substituted by a hydroxy or a phenyl group, or $R^1$ and $R^2$ together with the nitrogen atom they are attached to form a 5 to 8 membered ring optionally containing one or more further nitrogen, oxygen or sulfur atom(s) and said ring can be condensed with another alicyclic or heterocyclic ring, preferably a benzene, naphthalene, quinoline, isoquinoline, pyridine or pyrazoline ring, furthermore optionally the nitrogen and/or sulfur heteroatom(s) are present in the form of an oxide or dioxide, $R^3$ means a hydrogen atom, a phenyl group, a naphthyl group or a pyridyl group wherein said groups can be substituted by one or more halo atom(s) or $C_{1-4}$ alkoxy group(s), Y is a hydrogen atom, a hydroxy group, a $C_{1-24}$ alkoxy group optionally substituted by an amino group, a $C_{2-24}$ polyalkenyloxy group containing 1 to 6 double bond(s), a $C_{1-25}$ alkanoyl group, a $C_{3-9}$ alkenoyl group or a group of the formula $R^7$—COO— wherein $R^7$ represents a $C_{2-30}$ polyalkenyl group containing 1 to 6 double bonds(s), X stands for a halo atom, an amino group, a $C_{1-4}$ alkoxy group or X forms with B an oxygen atom, or X and Y together with the carbon atom they are attached to and the —NR—O—CH$_2$— group being between said carbon atoms form a ring of the formula a

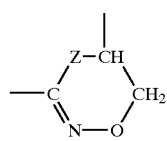
(a)

wherein

Z represents an oxygen atom or a nitrogen atom,

R stands for a hydrogen atom or

R forms with B a chemical bond,

A is a $C_{1-4}$ alkylene group or a chemical bond or a group of the formula b

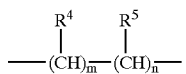
(b)

wherein $R^4$ represents a hydrogen atom, a $C_{1-5}$ alkyl group, a $C_{3-8}$ cycloalkyl group or a phenyl group optionally substituted by a halo atom, a $C_{1-4}$ alkoxy group or a $C_{1-5}$ alkyl group, $R^5$ stands for a hydrogen atom, a $C_{1-4}$ alkyl group or a phenyl group, m has a value of 0, 1 or 2, n has a value of 0, 1 or 2, or a physiologically acceptable acid addition salt thereof in admixture with one or more conventional carrier(s), wherein the antitumor activity is against tumors sensitive to the combination.

2. A pharmaceutical composition as claimed in claim 1, comprising paclitaxel as the active substance having antitumor activity.

3. A pharmaceutical composition as claimed in claim 1, comprising docetaxel as the active substance having antitumor activity.

4. A pharmaceutical composition as claimed in claim 1, comprising O-(3-piperidino-2-hydroxy-1-propyl)nicotinic amidoxime or a physiologically acceptable acid addition salt thereof as the hydroximic acid derivative of the formula I.

5. A pharmaceutical composition having antitumor activity with reduced side effect(s) comprising an enhanced effective amount of paclitaxel and O-(3-piperidino-2-hydroxy-1-propyl)-nicotinic amidoxime or a physiologically acceptable acid addition salt thereof, wherein said antitumor activity is against tumors sensitive to said composition.

6. A pharmaceutical composition having antitumor activity with reduced side effect(s) comprising an enhanced effective amount of docetaxel and O-(3-piperidino-2-hydroxy-1-propyl)-nicotinic amidoxime or a physiologically acceptable acid addition salt thereof, wherein said antitumor activity is against tumors sensitive to said composition.

7. A method for reducing the side effect(s) in a patient requiring a treatment for a tumor comprising administering an enhanced effective amount of a known active substance having antitumor effect selected from the group consisting of paclitaxel and docetaxel and an effective non-toxic amount of a hydroximic acid derivative of the formula I, wherein $R^1$, $R^2$, $R^3$, A, X, B, R and Y are as defined in claim 1, or a physiologically acceptable acid addition salt thereof to the patient, wherein said tumor is sensitive to said active substance; and the administration of the hydroximic acid derivative or a physiologically acceptable acid addition salt thereof reduces the side effects experienced by the patient requiring treatment for a tumor.

8. A method as claimed in claim 7, comprising administering paclitaxel as the active substance having antitumor activity.

9. A method as claimed in claim 7, comprising administering docetaxel as the active substance having antitumor activity.

10. A method as claimed in claim 7, comprising administering O-(3-piperidino-2-hydroxy-1-propyl)-nicotinic amidoxime or a physiologically acceptable acid addition salt thereof as the hydroximic acid derivative of the formula I.

11. A method as claimed in claim 7, comprising administering paclitaxel as the known active substance having antitumor activity and O-(3-piperidino-2-hydroxy-1-propyl)-nicotinic amidoxime or a physiologically acceptable acid addition salt thereof as the hydroximic acid derivative of the formula I.

12. A method as claimed in claim 7, comprising administering docetaxel as the known active substance having antitumor activity and O-(3-piperidino-2-hydroxy-1-propyl)-nicotinic amidoxime or a physiologically acceptable acid addition salt thereof as the hydroximic acid derivative of the formula I.

\* \* \* \* \*